United States Patent [19]

Bassler et al.

[11] Patent Number: 5,495,015
[45] Date of Patent: Feb. 27, 1996

[54] PROCESS FOR PRODUCING CAPROLACTAM THROUGH HYDROLYTIC CLEAVAGE OF MOLTEN POLYCAPROLACTAM

[75] Inventors: Peter Bassler, Viernheim; Michael Kopietz, Grünstadt, both of Germany

[73] Assignee: BASF Aktiengesellschaft, Ludwigshafen, Germany

[21] Appl. No.: 355,286

[22] Filed: Dec. 12, 1994

[51] Int. Cl.$^6$ ................................................. C07D 201/12
[52] U.S. Cl. ................................................. 540/540; 540/485
[58] Field of Search ...................... 540/540, 485

[56] References Cited

U.S. PATENT DOCUMENTS

| 3,563,980 | 2/1971 | Van Mourik et al. | 540/540 |
| 4,311,642 | 1/1982 | Crescentini et al. | 540/540 |
| 5,294,707 | 3/1984 | Kotek | 540/540 |

*Primary Examiner*—Robert T. Bond
*Attorney, Agent, or Firm*—Keil & Weinkauf

[57] ABSTRACT

Caprolactam is obtained from caprolactam-containing polymers in the presence of superheated water by bringing polymers which contain the repeating unit

—[—N(H)—(CH$_2$)$_5$—C(O)—]— or mixtures consisting essentially of

| from 40 to 99.9% | by weight of a polymer containing the repeating unit —[—N(H)—(CH$_2$)$_5$—C(O)—]—, |
| from 0.01 to 50% | by weight of additives selected from the group consisting of inorganic fillers, organic and inorganic pigments and dyes, |
| from 0 to 10% | by weight of organic and/or inorganic additives, |
| from 0 to 40% | by weight of non-polyamide-containing polymers and |
| from 0 to 60% | by weight of polyamides, with the exception of polycaprolactam and copolyamides prepared from caprolactam, | into contact with superheated water at from 280° to 320° C. and from 7.5 to 15 MPa and a weight ratio of water to polymer containing the repeating unit —[—N(H)—(CH$_2$)$_5$—C(O)—]— of from 5:1 to 13:1 and in a reaction time of less than 3 hours, with the proviso that the reaction mixture, consisting essentially of water and the polymer used or the mixture used, contains no gaseous phase under the conditions of the hydrolysis.

4 Claims, 1 Drawing Sheet

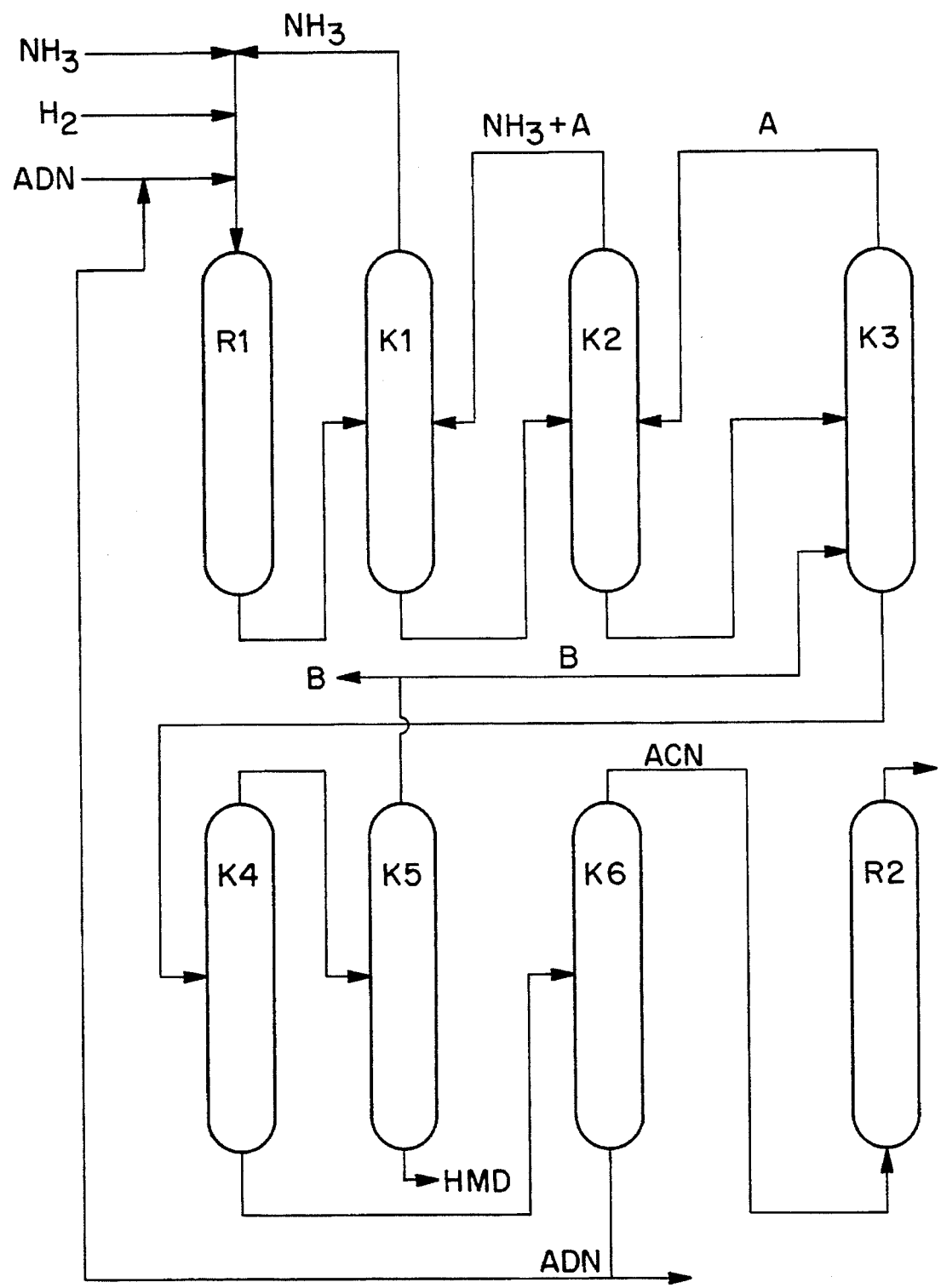

PROCESS FOR PRODUCING CAPROLACTAM THROUGH HYDROLYTIC CLEAVAGE OF MOLTEN POLYCAPROLACTAM

The present invention relates to an improved process for obtaining caprolactam from caprolactam-containing polymers in the presence of superheated water.

The present invention furthermore relates to an apparatus for carrying out the novel process and to the use of the novel process and of the novel apparatus for recycling polycaprolactam-containing wastes.

U.S. Pat. No. 4,605,762 describes a continuous process for the hydrolytic depolymerization of condensation polymers, in which waste material which is obtained during the production of articles from the condensation polymers is subjected to aqueous hydrolysis at from 200° to 300° C. and at a superatmospheric pressure of at least 15 atmospheres in a special apparatus. In the stated process, the hydrolysis is carried out using steam under high pressure. However, the hydrolysis of condensates which may contain fillers, such as glass fibers, or of blends is not described.

U.S. Pat. No. 3,939,153 describes a process for the preparation of caprolactam from polycaprolactam, in which a melt of the polymer and superheated steam are brought continuously into contact with one another at not less than 315° C. The disadvantage of this process is a low yield of not more than 20%.

It is an object of the present invention to provide a process for obtaining caprolactam from polymers containing, as a repeating unit,

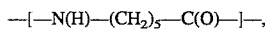

or from mixtures containing such polymers, which process gives higher yields of caprolactam in the absence of a catalyst. It is also intended to provide a process which makes it possible to utilize polycaprolactam-containing wastes which contain inorganic fillers to obtain caprolactam without having to accept a reduced yield.

We have found that this object is achieved by a process for obtaining caprolactam from caprolactam-containing polymers in the presence of superheated water, by bringing polymers which contain the repeating unit

—[—N(H)—(CH$_2$)$_5$—C(O)—]— or mixtures consisting essentially of

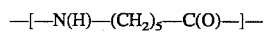

| | |
|---|---|
| from 40 to 99.9% | by weight of a polymer containing the repeating unit —[—N(H)—(CH$_2$)$_5$—C(O)—]—, |
| from 0.01 to 50% | by weight of additives selected from the group consisting of inorganic fillers, organic and inorganic pigments and dyes, |
| from 0 to 10% | by weight of organic and/or inorganic additives, |
| from 0 to 40% | by weight of non-polyamide-containing polymers and |
| from 0 to 60% | by weight of polyamides, with the exception of polycaprolactam and copolyamides prepared from caprolactam, | into contact with superheated water at from 280° to 320° C. and from 7.5 to 15 MPa, in a weight ratio of water to polymer containing the repeating unit —[—N(H)—(CH$_2$)$_5$—C(O)—]— of 5:1 to 13:1 and for a reaction time of less than 3 hours, with the proviso that the reaction mixture, consisting essentially of water and of the polymer used or of the mixture used, contains no gaseous phase under the conditions of the hydrolysis.

We have also found an apparatus for carrying out the novel process and the use of the novel process and of the novel apparatus for recycling polycaprolactam-containing waste.

According to the invention, the starting materials used are polymers which contain the repeating unit

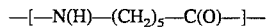

or are mixtures consisting essentially of

| | |
|---|---|
| from 40 to 99.99, | preferably from 70 to 90, % by weight of a polymer containing the repeating unit —[—N(H)—(CH$_2$)$_5$—C(O)—]— |
| from 0.01 to 50, | preferably from 4 to 10, % by weight of additives selected from the group consisting of inorganic fillers, organic and inorganic pigments and dyes, |
| from 0 to 10, | preferably from 0.1 to 5, % by weight of organic and/or inorganic additives, |
| from 0 to 40, | preferably from 5 to 25, % by weight of non-polyamide-containing polymers and |
| from 0 to 60, | preferably from 10 to 30, % by weight of polyamides, with the exception of polycaprolactam and copolyamides prepared from caprolactam. |

The polymer used is preferably polycaprolactam having a relative viscosity of from 1 to 10, preferably of from 2.0 to 4.0 (measured at a concentration of 1 g of polymer per 100 ml in 96% strength by weight sulfuric acid at 25° C.). It is also possible to use polycaprolactam which contains oligomers in an amount of from 0.01 to 10, preferably from 1 to 5, % by weight, based on the total amount. In principle, the novel process can also be carried out if oligomers of caprolactam are used instead of polycaprolactam.

Copolyamides obtained from caprolactam and other polyamide-forming monomers, for examples salts formed from a dicarboxylic acid, such as adipic acid, sebacic acid and terephthalic acid, and a diamine, such as hexamethylenediamine and tetramethylenediamine, preferably AH salt (obtained from adipic acid and hexamethylenediamine), and lactams, such as laurolactam, may also be used.

Observations to date have shown that all known polycaprolactams can be converted into caprolactam by the novel process, for example also a polycaprolactam which was prepared in the presence of mono- or dicarboxylic acids or amines, which act as chain regulators, for example acetic acid, propionic acid, benzoic acid, C$_4$–C$_{10}$-alkanedicarboxylic acids, such as adipic acid, pimelic acid, suberic acid, azelaic acid, sebacic acid, undecanedioic acid, dodecanedioioc acid and mixtures thereof, C$_5$–C$_8$-cycloalkanedicarboxylic acids, such as cyclopentane-1,3-dicarboxylic acid, cyclohexane-1,4-dicarboxylic acid and mixtures thereof, benzene- and naphthalenedicarboxylic acids which may carry up to two sulfo groups, including the corresponding alkali metal salts, and whose carboxyl groups are not adjacent, such as terephthalic acid, isophthalic acid, naphthalene-2,6-dicarboxylic acid, 5-sulfoisophthalic acid and their sodium and lithium salts, and mixtures thereof, and 1,4-piperazinedi-C$_1$–C$_6$-alkanedicarboxylic acids, such as 1,4-piperazinediacetic acid, 1,4-piperazinedipropionic acid, 1,4-piperazinedibutyric acid, 1,4-piperazinedipentanoic acid and 1,4-piperazinedihexanoic acid.

Corresponding copolyamides are known to a person skilled in the art and can be prepared by processes which are described, for example, in WO 93/25736, DE-A 14 95 198 and DE-A 25 58 480.

Observations to date have shown that all fillers, such as glass fibers, calcium carbonate and talc, which are usually used in the compounding of polyamides may be employed as inorganic fillers. Observations to date have shown that all pigments and dyes, such as titanium dioxide, cadmium sulfide, iron oxides or carbon blacks, which are usually used for coloring polyamides, and the conventional spinning dyes, such as chromium complexes or copper complexes, may be employed as inorganic and organic pigments and dyes.

The conventional stabilizers and antioxidants, heat stabilizers and UV stabilizers, antistatic agents and flameproofing agents may be used as organic and inorganic additives.

Antioxidants and heat stabilizers are, for example, sterically hindered phenols, hydroquinones, phosphites and derivatives and substituted members of this group and mixtures of these compounds, as well as copper compounds, such as copper(I) iodide and copper(II) acetate.

Examples of UV stabilizers are substituted resorcinols, silicylates, benzotriazoles, benzophenones and compounds of the HALS (hindered amine light stabilizer) type, and manganese(II) compounds are also suitable for this purpose.

The conventional substances, for example polyalkylene oxides and derivatives thereof, may be used as antistatic agents.

The conventional phosphorus and nitrogen/phosphorus containing compounds, such as esters of phosphoric acid, or phosphorous acid and of phosphonic and phosphinic acid and tertiary phosphines and phosphine oxides, such as triphenylphosphine oxide, phosphonitrile chloride, phosphoric ester amides, phosphoramides, phosphinamides, trisaziridinylphosphine oxide and tetrakis(hydroxymethyl)phosphonium chloride, may be used as flameproofing agents.

The conventional thermoplastic engineering polymers, such as polymers based on ethylene, propylene and styrene, and copolymers thereof with butadiene and acrylonitrile (ABS plastics), may be used as non-polyamide-containing polymers.

Suitable polyamides with the exception of polycaprolactam and copolyamides prepared from caprolactam are, for example, polyamide 66, polyamide 610 and polyamide 46.

Preferred starting materials are polycaprolactam which contains inorganic fillers, in particular glass fibers, and is to be disposed of, and wastes which are obtained in the production of polycaprolactam and in the processing thereof to give filaments, films and injection-molded or extruded parts, and shaped utility articles, such as films, packaging, fabric, carpet fibers, filaments and extruded parts, which are to be disposed of.

According to the invention, the abovementioned polymers or mixtures are brought into contact with superheated water which is at from 280° to 320° C., preferably from 295° to 310° C., particularly preferably from 300° to 305° C., and at from 7.5 to 15, preferably from 10 to 15, particularly preferably from 10 to 12, MPa, the weight ratio of water to the polymer containing the repeating unit —[—N(H)—(CH$_2$)$_5$—C(O)—]— being chosen in the range from 5:1 to 13:1, preferably from 8:1 to 13:1. Furthermore, according to the invention, the reaction time is chosen to be less than 3 hours, preferably from 15 to 90, particularly preferably from 30 to 60, minutes.

Choosing the conditions of the hydrolysis within the stated values so that the reaction mixture, consisting essentially of water and the polymer used or the mixture used, contains no gaseous phase is essential for the success of the novel process. Observations to date have shown that gaseous fractions in the reation mixture lead to lower yields.

The reaction mixture obtained after the hydrolysis can be worked up in the usual manner, for example by separating caprolactam from any solids present, such as glass fibers, fillers, pigments, etc., and feeding it to a further purification stage, preferably a distillation.

The caprolactam obtained by the novel process can of course be converted back into polycaprolactm or into corresponding copolymers and blends.

In a preferred embodiment, the abovementioned polymers or mixtures are melted by heating them to 250°–350° C., preferably 290°–300° C. The resulting melt is compressed, subsequently or preferably simultaneously, to a pressure of from 7.5 to 30, preferably from 10 to 15, MPa, the pressure advantageously being chosen so that it is slightly above the pressure of the superheated water with which the melt (melt A) is subsequently brought into contact, in order thus to prevent the superheated water from flowing back into the melting apparatus (1). In a particularly preferred embodiment, the melting process and the compression are carried out simultaneously in a conventional extruder as melting apparatus (1).

BRIEF DESCRIPTION OF THE DRAWING

The drawing schematically sets forth preferred apparatus for carrying out the process.

The superheated water and the melt (melt A) compressed in the melting apparatus (1) are then brought into contact in a hydrolysis reactor (2). According to the invention, the temperatures and the pressure range are chosen so that no gaseous phase is present, in particular during the hydrolysis in the hydrolysis reactor. Here, the temperatures are in general from 280° to 320° C., preferably from 290° to 310° C., particularly preferably from 300° to 305° C., and the pressure is, as a rule, from 7.5 to 15, preferably from 10 to 12, MPa. The residence time in the hydrolysis reactor depends essentially on the amount of water added, based on the repeating unit —[N(H)—(CH$_2$)$_5$—C(O)—]—, and is usually from 15 to 90, preferably from 30 to 60, minutes.

Pressure-resistant tubes may be used as hydrolysis reactor (2), and said reactor may or may not be provided with baffles, such as mixing elements of the type SMX from Sulzer (cf. Chem.-Ing.-Tech. 62 (1990) 650–654). In a preferred embodiment, a tube reactor having an L/D ratio of from 20:1 to 150:1, preferably from 50:1 to 120:1, is used.

In a preferred embodiment, the mixture discharged from the hydrolysis reactor is fed into a let-down apparatus (3) which may be a single-stage or two-stage apparatus, essentially two phases being formed as a result of the pressure drop to 0.1–1.6, preferably 0.1–0.4, kPa: a gaseous phase B, which contains essentially water and may contain small amounts of other volatile substances, such as caprolactam and traces of volatile amine compounds, and a nongaseous phase C which contains essentially the main amount of cleaved caprolactam and, depending on the mixture used, may contain additives, such as glass fibers, pigments, additives, etc. The gaseous and steam-containing phase B is usually separated from the nongaseous phase C in a let-down apparatus (3), the water preferably being separated off in a suitable apparatus, for example in a distillation apparatus or an evaporator stage, and then being mixed with the water which is introduced into the hydrolysis reactor (2) for hydrolyzing the polymers or mixtures.

The nongaseous phase C, which as a rule contains water and may contain additives, organic and inorganic additives, non-polyamide-containing polymers and polyamides, with the exception of polycaprolactam and copolyamides prepared from caprolactam, and generally contains from 5 to 20% by weight of caprolactam, is fed, in a preferred embodiment, into a separation apparatus (4), in which any insoluble components present, such as additives, for example glass fibers, pigments, other polymers, etc., are removed.

The separation apparatus (4) used may be a conventional filter apparatus, such as a belt filter or a back-washable tube filter, or another conventional apparatus which permits continuous or periodic discharge, preferably a belt filter or a back-washable tube filter.

The solution freed from insoluble components can then be worked up by methods known per se, for example by separating the water from caprolactam by distillation and adding it to the hydrolysis water, similarly to the working up of the gaseous phase B, and feeding the caprolactam to a purification stage, for example the purification stage for crude caprolactam in an existing caprolactam plant. Other possibilities for, if desired, purifying the caprolactam obtained according to the invention are disclosed, for example, in EP-A 568,882 and 570,843. The purified caprolactam is then in general available for further use, in particular for the preparation of PA 6.

According to the invention, the novel process is used for recycling polycaprolactam-containing wastes, such as used carpets, carpet offcuts, polyamide 6 production wastes and polyamide mixtures which may contain up to 60% by weight of polyamides which were not prepared from caprolactam.

The advantages of the novel process over prior art processes are the cleavage yields of up to 96%, short residence times and smaller amounts of solvents and wastes which require treatment and disposal.

EXAMPLES

Example 1

0.3 kg/hour of polycaprolactam (Ultramid® BS 700, having a relative viskosity of 2.7, measured in a 1% strength by weight solution in 96% strength by weight sulfuric acid at 23° C. maintained at 270° C. and under a pressure of 20 MPa and 2.7 kg/hour of water maintained at 290° C. and a pressure of 12 MPa were fed into a 3 l tube reactor (length/diameter ratio: 110:1). The average residence time was 60 minutes. After leaving the reactor, the mixture was cooled to 115° C. and let down to 0.1 kPa. The reaction mixture obtained was analyzed by gas chromatography. The results are shown in the table below.

Examples 2 to 11

Example 1 was repeated at different water-to-polymer ratios and different temperatures. The results are summarized in the table below.

TABLE

| Example | Weight ratio of H$_2$O: polycaprolactam | Temperature [°C.] | Pressure [MPa] | Residence time [min] | Yield of caprolactam [%] |
|---------|------------------------------------------|-------------------|----------------|----------------------|--------------------------|
| 1  | 10.2:1 | 290 | 12.0 | 35 | 75   |
| 2  | 10.6:1 | 292 | 12.0 | 51 | 92.5 |
| 3  | 10.0:1 | 296 | 12.0 | 54 | 93.6 |
| 4  | 10.4:1 | 296 | 12.0 | 60 | 94   |
| 5  | 8.0:1  | 300 | 12.0 | 70 | 92   |
| 6  | 8.3:1  | 300 | 12.0 | 68 | 90.1 |
| 7  | 11.0:1 | 305 | 12.0 | 60 | 96   |
| 8  | 11.0:1 | 300 | 12.0 | 55 | 95.9 |
| 9  | 13.0:1 | 300 | 12.0 | 55 | 96.4 |
| 10 | 11.0:1 | 320 | 13.0 | 50 | 85   |
| 11 | 10.0:1 | 300 | 13.0 | 90 | 80   |

We claim:

1. A process for obtaining caprolactam from caprolactam-containing polymers in the presence of superheated water, which comprises contacting polymers which contain the repeating unit

—[—N(H)—(CH$_2$)$_5$—C(O)—]— or mixtures consisting essentially of

| from 40 to 99.9% | by weight of a polymer containing the repeating unit —[—N(H)—(CH$_2$)$_5$—C(O)—]—, |
| from 0.01 to 50% | by weight of additives selected from the group consisting of inorganic fillers, organic and inorganic pigments and dyes, |
| from 0 to 10% | by weight of organic or inorganic additives, |
| from 0 to 40% | by weight of non-polyamide-containing polymers and |
| from 0 to 60% | by weight of polyamides, with the exception of polycaprolactam and copolyamides prepared from caprolactam, | with superheated water at from 280° to 320° C. and at from 7.5 to 15 MPa and a weight ratio of water to polymer containing the repeating unit —[—N(H)—(CH$_2$)$_5$—C(O)—]— of 5:1 to 13:1 and in a reaction time of less than 3 hours, with the proviso that the reaction mixture, consisting essentially of water and the polymer used or the mixture used, contains no gaseous phase under the conditions of the hydrolysis.

2. The process of claim 1, wherein the following steps are carried out:
   (a) melting and compression of the polymer or of the mixture at from 250° to 350° C. and to a pressure of from 7.5 to 30 MPa to give a melt A,
   (b) mixing of water maintained at from 280° to 320° C. and from 7.5 to 15 MPa with the melt A in a hydrolysis reactor,
   (c) discharge of a nongaseous phase leaving the hydrolysis reactor, with flash evaporation to give a gaseous phase B and a nongaseous phase C,
   (d) separating off any nonliquid fractions in the nongaseous phase C to give a liquid phase D, containing caprolactam, and a solid phase E and
   (e) optionally, transfer of the liquid phase D obtained in stage d) to a purification stage for caprolactam.

3. A process as defined in claim 1, wherein oligomers which contain the repeating unit —[—N(CH)—(CH$_2$)$_5$—C(O)—]— are used instead of polymers which contain the repeating unit

—[—N(H)—(CH$_2$)$_5$—C(O)—]—.

4. A process as defined in claim 1, wherein the polymers or mixtures are contacted with superheated water which is at a temperature of from 300°–305° C. and under a pressure of 10 to 12 MPa, and wherein the ratio of water to the polymer containing the repeating unit —[—N(H)—(CH$_2$)$_5$—C(O)—]— is from 8:1 to 13:1 and wherein the reaction time is from 30 to 60 minutes.

* * * * *